United States Patent [19]
Golden et al.

[11] Patent Number: 5,425,382
[45] Date of Patent: Jun. 20, 1995

[54] APPARATUS AND METHOD FOR LOCATING A MEDICAL TUBE IN THE BODY OF A PATIENT

[75] Inventors: Robert N. Golden; Fred E. Silverstein, both of Seattle, Wash.

[73] Assignee: University of Washington, Seattle, Wash.

[21] Appl. No.: 121,929

[22] Filed: Sep. 14, 1993

[51] Int. Cl.$^6$ .............................................. A61B 5/05
[52] U.S. Cl. .................................................. 128/899
[58] Field of Search ...................... 128/630, 631, 653.1, 128/653.4, 654, 899, 903, 772, 200.26, 207.14, 207.15; 600/12; 324/207.17, 207.26, 329, 231; 340/572, 537

[56] References Cited

U.S. PATENT DOCUMENTS

| | | | |
|---|---|---|---|
| 3,757,773 | 9/1973 | Kolin | 128/2.05 F |
| 4,063,561 | 12/1977 | McKenna | 128/351 |
| 4,244,362 | 1/1981 | Anderson | 128/200.26 |
| 4,249,536 | 2/1981 | Vega | 128/349 B |
| 4,317,078 | 2/1982 | Weed et al. | 324/207.26 |
| 4,402,310 | 9/1983 | Kimura | 128/4 |
| 4,608,992 | 9/1986 | Hakim et al. | 128/654 |
| 4,619,247 | 10/1986 | Inoue et al. | 128/6 |
| 4,671,287 | 6/1987 | Fiddian-Green | 128/631 |
| 4,790,809 | 12/1988 | Kuntz | 604/8 |
| 4,809,713 | 3/1989 | Grayzel | 128/785 |
| 4,913,139 | 4/1990 | Ballew | 128/200.11 |
| 4,943,770 | 7/1990 | Ashley-Rollman et al. | 324/207.17 |
| 5,099,845 | 3/1992 | Besz et al. | 128/653.1 |
| 5,134,370 | 7/1992 | Jefferts et al. | 340/573 |
| 5,257,636 | 11/1993 | White | 128/653.1 |

FOREIGN PATENT DOCUMENTS

| | | |
|---|---|---|
| 0302001A1 | 7/1988 | European Pat. Off. . |
| 2903357A1 | 7/1980 | Germany . |
| 4014947A1 | 11/1991 | Germany . |

OTHER PUBLICATIONS

Williams et al. abstract, "The Localisation of Enteral Tubes Using a Novel Non-Radiological Technique," *British Society of Gastroenterology* (Mar. 1992).

Gaston et al., "Experimental Studies in Dogs and Prospects of Application," *Journal of Neuroradiology* 15(2):137–147, 1988.

Ram and Meyer, "Heart Catheterization in a Neonate by Interacting Magnetic Fields: A New and Simple Method of Catheter Guidance," *Catheterization and Cardiovascular Diagnosis* 22:317–319 (1991).

*Primary Examiner*—Lee S. Cohen
*Assistant Examiner*—Brian M. Green
*Attorney, Agent, or Firm*—Seed and Berry

[57] ABSTRACT

There is disclosed an apparatus and method for locating a medical tube within the body of a patient. The medical tube is located by a detection apparatus which senses the static magnetic field strength gradient generated by a magnet associated with the medical tube and indicates the value of the gradient to the user. The detection apparatus is moved about the body of the patient until the greatest gradient magnitude is indicated. The detection apparatus distinguishes the field strength of the magnet associated with the medical tube from the earth's field strength by sensing the magnet's field strength at two different distances from the magnet.

17 Claims, 4 Drawing Sheets

APPARATUS AND METHOD FOR LOCATING A MEDICAL TUBE IN THE BODY OF A PATIENT

TECHNICAL FIELD

This invention is generally directed to an apparatus and method for detecting the location of a medical tube within the body of a patient and, more specifically, to detecting the location of a medical tube using a detection apparatus which senses a static magnetic field strength gradient generated by a magnet associated with the medical tube.

BACKGROUND OF THE INVENTION

There are many instances in clinical medicine where detecting the location of a medical tube within a patient is important. For example, when positioning feeding tubes through the mouth or nose of a patient, it is essential that the end of the feeding tube pass into the patient's stomach, and that it does not "curl up" and remain in the esophagus. If the end of the feeding tube is not properly positioned within the stomach, aspiration of the feeding solution into the patient's lungs may occur. In addition to feeding tubes, a variety of other medical tubes require accurate positioning within a patient's body, including dilating tubes to widen an esophageal stricture, tubes for measuring pressure waves in the stomach and esophagus of a patient who is suspected of having esophageal motor disorders, Sengstaken-Blakemore tubes in the stomach and esophagus of a patient to control bleeding from varicose veins in the esophagus, colonic decompression tubes in the colon of a patient to assist in relieving distention of the colon by gas, urologic tubes in the bladder, ureter or kidney of a patient, and vascular tubes in the heart or pulmonary arteries of a patient.

Currently, the location of a medical tube within the body of a patient is routinely detected by the use of imaging equipment, such as a chest or abdominal X-ray. However, such a procedure requires transportation of the patient to an X-ray facility or, conversely, transportation of the X-ray equipment to the patient. This is both inconvenient and costly to the patient, and is particularly stressful in those instances where the patient repeatedly and inadvertently removes a medical tube, such as a feeding tube, thus requiring repeated reinsertion and X-rays.

Prior attempts at detecting the location of medical tubes within a patient have met with only limited success. For example, in U.S. Pat. No. 5,099,845 to Besz et al., a transmitter is located within a catheter, and an external receiver, tuned to the frequency of the transmitter, is used to detect the location of the catheter within the patient. This approach, however, requires either an external or internal power source to drive the transmitter. An external power source adds significant risk associated with shock or electrocution, and requires that electrical connections be made prior to positioning of the catheter within the patient. An internal power source, such as a battery, must be relatively small and can only provide power to the transmitter for a limited time. This precludes long-term detection of the catheter's location, and poses additional risks associated with placing a battery internally in a patient, such as the risk of battery leakage or rupture. In addition, the transmitter is relatively complex, and requires an active electronic circuit (either internal or external to the catheter), as well as the various wires and connections necessary for its proper function. Lastly, the signal produced by the transmitter is attenuated differently by different body tissues and bone. This attenuation requires adjustments in the transmitter's signal strength and frequency depending on the location of the catheter within the patient's body.

A further attempt at detecting the location of medical tubes within a patient is disclosed in U.S. Pat. No. No. 4,809,713 to Grayzel. There, an electrical cardiac-pacing catheter is held in place against the inner heart wall of a patient by the attraction between a small magnet located in the tip of the pacing catheter and a large magnet located on (e.g., sewn into) the patient's chest wall. An indexed, gimbaled, three-dimensional compass is used to determine the best location for the large magnet. The compass' operation relies upon the torque generated by the magnetic forces between the small magnet and the magnetized compass pointer in order to point the compass towards the small magnet. However, this compass will simultaneously try to orient itself to the earth's ambient magnetic field. Because of this, the forces between the small magnet and the magnetized compass pointer at distances greater than several centimeters are not strong enough to accurately orient the compass towards the small magnet. Furthermore, although the compass aids positioning of the large magnet, positioning of the small magnet, and hence the pacing catheter, still requires the use of imaging equipment, such as X-ray or ultrasound.

For the foregoing reasons, there is a need in the art for an apparatus and method for detecting the location of a medical tube within the body of a patient which avoids the problems inherent in existing techniques. The apparatus and method should provide for the detection of the medical tube at distances ranging from several centimeters to several decimeters, should not require the medical tube to have an internal or external power source, and should obviate the need to independently verify positioning of the medical tube with imaging equipment.

SUMMARY OF THE INVENTION

Accordingly, it is an object of the present invention to provide an apparatus and method for detecting the location of a medical tube within the body of an animal patient (including humans) without the aid of imaging equipment, particularly X-ray. It is a further object to detect the location of the medical tube without relying upon torque generated by the magnetic forces between the medical tube and the detection apparatus. Yet, a further object is to detect the location of the medical tube while dynamically nulling sensing of the earth's ambient magnetic field, and to thereby allow detection distances suitable for locating a wide variety of medical tubes at any location within the body of the patient.

The present invention satisfies these objectives by providing an apparatus and method for detecting the location of a magnet associated with a medical tube within the body of a patient. In one aspect of this invention, the apparatus of this invention comprises a first and second means for sensing a first and second static magnetic field strength, respectively, at first and second distances from the magnet, respectively, where the second distance is greater than the first; means for providing a first detection signal, which is a function of the first static magnetic field strength; means for providing a second detection signal, which is a function of the second static magnetic field strength; means for providing a differential signal, which is a function of the difference between the first and second detection signals; and means for indicating a value for the differential signal.

The first and second sensing means also provide, respectively, a first sensor signal, which is a function of the first static magnetic field strength, and a second sensor signal, which is a function of the second static magnetic field strength. The means for providing the first detection signal receives the first sensor signal, and the means for providing the second detection signal receives the second sensor signal. Finally, the means for providing the differential signal receives the first and second detection signals, and the means for indicating the differential signal's value receives the differential signal.

By sensing the static magnetic field strength of the magnet associated with the medical tube, the present invention obviates the need for imaging equipment, such as X-ray, to verify positioning of the medical tube. Also, by sensing the magnet's field strength at two different distances (i.e., the first and second distances) from the magnet between which the magnet's field strength will have a gradient and the earth's field strength will not, and by indicating the gradient to the user, the present invention dynamically nulls sensing of the earth's ambient magnetic field. This nulling allows the magnet to be sensed at distances ranging from several centimeters to several decimeters, which makes the detection apparatus suitable for locating the medical tube at any location within the patient's body.

In one embodiment of this invention, the first and second sensing means comprise a static magnetic field strength sensor driver, and first and second static magnetic field strength sensors. The driver provides a driver signal which causes the sensors to provide the first and second sensor signals. In a preferred embodiment, the driver comprises an oscillator and output transistors, wherein the output transistors are alternately switched by the oscillator and are thereby caused to provide the driver signal. The sensors each comprise a flux-gate toroidal sensor, which includes an excitation winding which receives a driver signal, and a detection winding which provides the respective sensor signal. By providing a driver signal which causes the sensors to provide the first and second sensor signals, the present invention does not need to rely upon magnetic forces between the magnet and the apparatus for detecting the location of the medical tube.

In another embodiment, the detection apparatus further comprises a means for automatically controlling, monitoring, and calibrating (a) the first and second means for sensing the first and second static magnetic field strengths; (b) the means for providing the first detection signal; (c) the means for providing the second detection signal; (d) the means for providing the differential signal; and (e) the means for indicating the differential signal's value. In a preferred embodiment, the automatic controlling, monitoring, and calibrating means is a microprocessor.

In another aspect of this invention, the apparatus of this invention comprises the static magnetic field strength sensor driver, the first and second static magnetic field strength sensors, first and second amplifiers, first and second integrators, a differential amplifier, a magnitude circuit, a visual display driver, and a visual display.

The first amplifier receives the first sensor signal and provides a first amplified signal which is proportional to the first sensor signal. Similarly, the second amplifier receives the second sensor signal and provides a second amplified signal which is proportional to the first sensor signal.

The first and second integrators receive the first and second amplified signals, respectively, and provide the first and second detection signals, respectively. The differential amplifier receives the first and second detection signals and provides the differential signal.

Further, the magnitude circuit receives the differential signal and provides a magnitude signal which is proportional to the magnitude of the differential signal. The visual display driver receives the magnitude signal and provides a visual display signal. The visual display receives and visually indicates the visual display signal.

In a preferred embodiment, the visual display driver comprises a light emitting diode bar array driver, and the visual display comprises a light emitting diode bar array.

In another preferred embodiment, the apparatus further comprises a tone generator for receiving the magnitude signal and providing a tone signal which is a function of the magnitude signal, and a speaker for receiving and audibly indicating the tone signal.

In still another preferred embodiment, the apparatus further comprises a polarity circuit for receiving the differential signal and providing a polarity signal which is a function of the polarity of the differential signal, a polarity display driver for receiving the polarity signal and providing a polarity display signal, and a polarity display for receiving and visually indicating the polarity display signal.

In still another preferred embodiment, the apparatus further comprises the microprocessor for automatically controlling, monitoring and calibrating the static magnetic field strength sensor driver, the first amplifier, the second amplifier, the differential amplifier and the visual display driver.

In still another aspect of this invention, a method for detecting the location of a magnet associated with a medical tube within the body of a patient comprises the following steps: sensing the first and second static magnetic field strengths at the first and second distances; providing the first and second sensor signals; receiving the first and second sensor signals and providing the differential signal; receiving and indicating the value of the differential signal; and determining the location of the medical tube by varying the first and second distances until the greatest value is indicated.

In still another aspect of this invention, a method of verifying the location of a magnet associated with the end of a medical tube within the body of a patient comprises the following steps: sensing the first and second static magnetic field strengths at the first and second distances; providing the first and second sensor signals; receiving the first and second sensor signals and providing the differential signal; receiving and indicating the polarity of the differential signal; and manipulating the magnet until the indicated polarity changes.

These and other features of the present invention will be better understood with reference to the following detailed description, appended claims and accompanying drawings.

DETAILED DESCRIPTION OF THE INVENTION

Figure 1A:
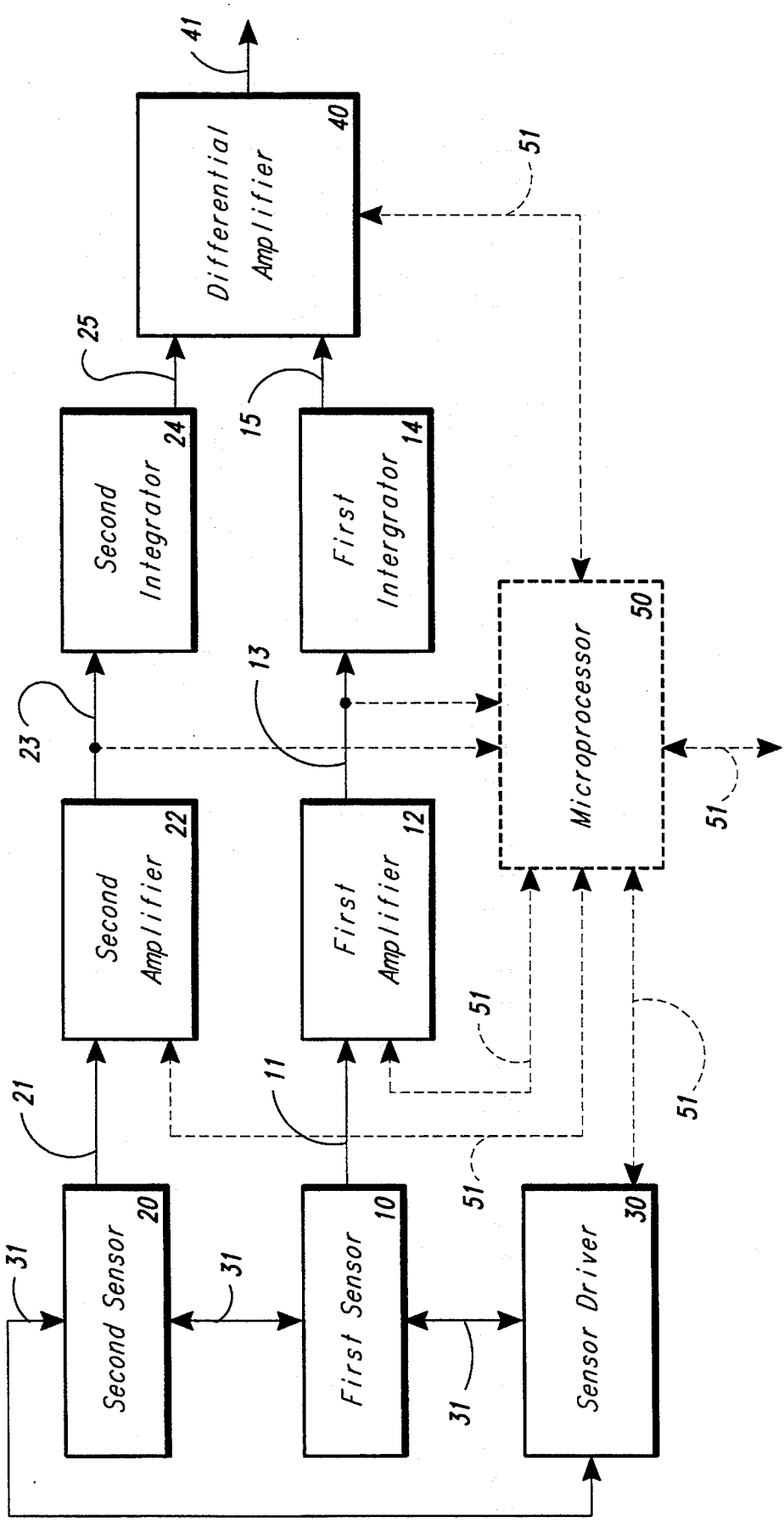
FIG. 1(a) and 1(b) are block diagrams illustrating the structure and operation of a representative detection apparatus of this invention.

The present invention provides an apparatus and method for detecting the location of a medical tube within the body of a patient. As used herein, the term "medical tube" means any type of tube or device which may be inserted into a patient's body, including (but not limited to) catheters, guide wires, and medical instruments. For example, catheters include such items as feeding tubes, urinary catheters, guide wires and dilating catheters, as well as nasogastric tubes, endotracheal tubes, stomach pump tubes, wound drain tubes, rectal tubes, vascular tubes, Sengstaken-Blakemore tubes, colonic decompression tubes, pH catheters, motility catheters, and urological tubes. Guide wires are often used to guide or place dilators and other medical tubes. Medical instruments include endoscopes and colonoscopes. In short, the location of any foreign object within a patient's body is a suitable device for detection by the present invention, and is encompassed within the term "medical tube".

The present invention detects the location of the medical tube by sensing the static magnetic field strength gradient produced by a permanent magnet associated with the medical tube. As used herein, the term "associated with" means permanently fixed, removably attached, or in close proximity to, the medical tube. In one embodiment, such as a feeding tube, the magnet is associated with the end of the medical tube. In another embodiment, such as a Sengstaken-Blakemore tube, the magnet is associated with the medical tube at a location above the gastric balloon. Preferably, the magnet is a small, cylindrical, rotatably attached, rare-earth magnet. Suitable magnets include rare earth magnets such as samarium cobalt and neodymium iron boron, both of which generate high field strengths per unit volume. While magnets which generate a high field strength for their size are preferred, weaker magnets such as Alnico or ceramic may also be utilized.

Since the magnet of this invention is permanent, it requires no power source. Accordingly, the magnet maintains its magnetic field indefinitely, which allows long-term positioning and detection of medical tubes without the disadvantages associated with an internal or external power source. In particular, by avoiding the use of a power source, the undesirable electrical connections necessary for the use of a power source are avoided. Thus, there is no risk of shock to (or possible electrocution of) the patient. Furthermore, the magnet's static magnetic field passes unattenuated through body tissue and bone. This property allows the use of the present invention to detect the medical tube at any location within the patient's body.

The magnet, and hence the medical tube, is detected using a detection apparatus which contains at least two static magnetic field strength sensors configured geometrically to null detection of ambient, homogeneous magnetic fields (e.g., the earth's field), while still detecting the magnetic field strength gradient produced by the magnet. The detection apparatus is an active, electronic instrument, and can detect the relatively small magnetic field strength gradient produced by the magnet at distances ranging from several centimeters to several decimeters, and preferably from about 2 centimeters to about 3 decimeters. It also indicates the value of the gradient, thus allowing the user to accurately determine the location of the magnet, and hence the medical tube. In a preferred embodiment, the detection apparatus indicates the value of the gradient as both a magnitude and a polarity. By manipulating the magnet until the indicated polarity changes, detection of the location of the medical tube can be verified. Such manipulation of the magnet can be accomplished either by means of an attached guide wire, or by rotating the medical tube itself.

Due to the sensitivity of the apparatus of the present invention to the magnet's field strength gradient, additional imaging equipment is not necessary to detect the location of the medical tube. Accordingly, the present invention is suitable for use in environments which lack such equipment. For example, nursing homes rarely have X-ray equipment on-site, and the apparatus and method of the present invention is particularly suited for use in such facilities.

Figure 1B:
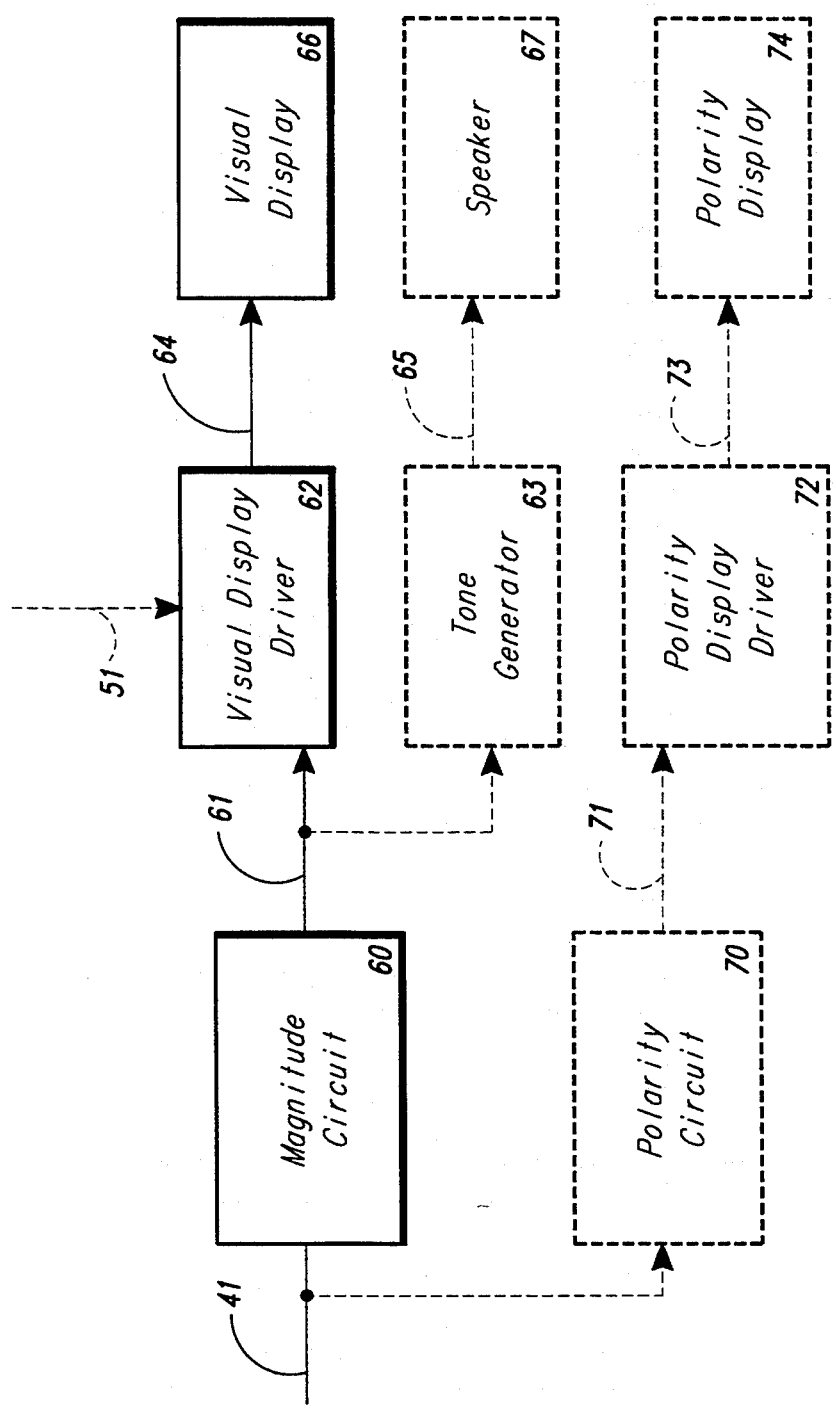

Referring to FIG. 1(a) and 1(b), a block diagram illustrating the structure and operation of a representative detection apparatus of this invention is shown. In FIG. 1(a), a static magnetic field strength sensor driver (30) provides a first static magnetic field strength sensor (10) and a second static magnetic field strength sensor (20) with a driver signal (31), thereby causing the first sensor (10) to provide a first sensor signal (11) and the second sensor (20) to provide a second sensor signal (21).

The first and second sensor signals (11) and (21) are functions of a first and second static magnetic field strength, respectively, sensed at a first and second distance, respectively, from the magnet. The first sensor (10) and the second sensor (20) are separated by a distance equal to the difference between the first and second distances. In this geometric configuration, while an ambient magnetic field strength (such as the earth's field strength) will have an equivalent value when sensed by either sensor (10) or (20), the magnet's magnetic field strength will have a different value depending on whether it is sensed by the first sensor (10) or the second sensor (20). By subtracting the field strength sensed at one sensor from the field strength sensed at the other, the magnet's field strength gradient can be sensed while at the same time nulling sensing of the earth's field strength. Several different types of sensors may be used in the practice of this invention, including (but not limited to) Hall-effect, flux-gate, squid, magneto-resistive, and nuclear precession sensors. In addition, a plurality of sensors may be employed.

A first amplifier (12) receives the first sensor signal (11) and provides a first amplified signal (13) which is proportional to the first sensor signal (11). Similarly, a second amplifier (22) receives the second sensor signal (21) and provides a second amplified signal (23) which is proportional to the second sensor signal (21). In a preferred embodiment, the proportionality constant between the amplified signals (13) and (23) and the sensor signals (11) and (21) (i.e., the gain of the amplifiers (12) and (22)) will be variable, either automatically or manually, to maintain appropriate sensitivity as the detection apparatus approaches the magnet.

A first integrator (14) receives the first amplified signal (13) and provides a first detection signal (15), which is the integral of the first amplified signal (13). Likewise, a second integrator (24) receives the second amplified signal (23) and provides a second detection signal (25), which is the integral of the second amplified signal (23). Because the integrals of the amplified signals (13) and (23), and hence the sensor signals (11) and (21), are proportional to the sensed first and second field strengths, the detection signals (15) and (25) are proportional to the sensed first and second field strengths.

A differential amplifier (40) receives the detection signals (15) and (25) and provides a differential signal (41) which is a function of the difference between the detection signals (15) and (25). In the absence of any sensed magnetic field strength gradient, the differential signal (41) from the differential amplifier (40) has a value of zero. When the detection apparatus is brought in close proximity to the magnet, the sensed value of the gradient between the sensors (10) and (20) is non-zero, and therefore the value of the differential signal (41) is non-zero. The polarity of the value (i.e., positive or negative) depends upon the orientation of the sensed magnet.

Referring to FIG. 1(b), a magnitude circuit (60) receives the differential signal (41) and provides a magnitude signal (61) which is proportional to the magnitude of the differential signal (41). A visual display driver (62) then receives the magnitude signal (61) and provides visual display signals (64) to a visual display (66). In a preferred embodiment, the visual display (66) displays a continuous analog representation of the magnet's magnetic field strength gradient, including its magnitude and polarity. Such a representation can be made with a light-emitting diode bar array or a liquid crystal display. In addition, a speaker (67) may optionally be employed. A tone generator (63) receives the magnitude signal (61) and provides a tone signal (65) to the speaker (67). The tone signal (65) is a function of the magnitude signal (61). The sound projected by the speaker (67) may change in volume or pitch corresponding to the magnitude signal (61). Such a visual display (66) and/or speaker (67) allows the user to move or sweep the detection apparatus over the patient's body and to quickly determine the nearest external point to the location of the internal magnet associated with the medical tube.

In a further embodiment, an optional polarity circuit (70) receives the differential signal (41) and provides a polarity signal (71) which is a function of the polarity of the differential signal (41). A polarity display driver (72) then receives the polarity signal (71) and provides a polarity display signal (73) to a polarity display (74). In this embodiment, the magnet is preferably made of neodymium iron boron (NdFeB), and is a small cylinder with dimensions on the order of 0.10 inches in diameter and 0.25 to 0.5 inches in length. The magnet is magnetized parallel to the diameter or transverse axis—that is, the north and south magnetic poles are half cylinders. This form of magnetization provides the greatest field strength at a given distance for such a cylindrical magnet. In addition, this magnet configuration allows the user to verify that the detection apparatus is sensing the magnet. Specifically, the user can rotate the magnet by, for example, manually rotating the medical tube. Such rotation about the longitudinal axis causes the sensed polarity to change. This change is indicated by the detection apparatus to the user. Alternatively, rather than rotating the medical tube, the magnet may be rotatably fixed to the medical tube such that the user may rotate the magnet by, for example, rotating a guide wire running down the medical tube and attached to the magnet.

Referring to FIG. 1(a) and 1(b), an optional microprocessor (50) receives the amplified signals (13) and (23), and receives and provides control, monitoring, and calibration signals (51) from and to the sensor driver (30), the first and second amplifiers (12) and (22), the differential amplifier (40), and the visual display driver (62). It should be understood that the microprocessor (50) and its accompanying software may be the only digital element of an otherwise analog embodiment of the present invention, it may be an element in a mixed-mode embodiment, or it may be a digital element in a fully digital embodiment.

The apparatus of the present invention can detect the location of a wide variety of medical tubes. For example, a Sengstaken-Blakemore tube is sometimes inserted into the stomach and esophagus of a patient to stop bleeding from severe esophageal varices. Such a tube is a multilumen tube with a suction tube in the stomach to detect bleeding, a gastric balloon in the proximal stomach to act as an anchor to hold the tube in place and to press on varices at the junction between the esophagus and stomach, an esophageal balloon to press on the varices directly and stop the bleeding, and a suction tube above the esophageal balloon to remove saliva and blood. By placing a magnet between the esophageal and gastric balloons, the present invention may be used to detect the magnet, and hence the position of the medical tube within the patient.

As a medical tube is inserted into a patient, the location of the magnet can be sensed by moving the detection apparatus over the surface of the patient's body and watching the visual display. As the sensors approach the magnet inside the patient, the display will indicate a greater magnitude, by increasing the height of the display bar graph, and by increasing the volume or pitch of the sound projected by the speaker. Also, after initial tube positioning, the location of the magnet can be similarly verified at any time.

Although the present invention has been described in detail, with reference to certain preferred embodiments, other embodiments are possible. For example, one skilled in this art would understand that the invention may be implemented with analog, mixed-mode, or digital elements, and with either discrete components or integrated circuits, or both. Furthermore, the following specific examples are offered by way of illustration, not limitation.

EXAMPLES

Detection Apparatus

Example 1

In this representative embodiment, the detection apparatus includes a pair of flux-gate toroidal sensors, their sensor driver, amplifiers, integrators, a differential amplifier, a magnitude circuit, a visual display driver, a visual display, a tone generator, a speaker, a polarity circuit, a polarity display driver, and a polarity display.

Figure 3:
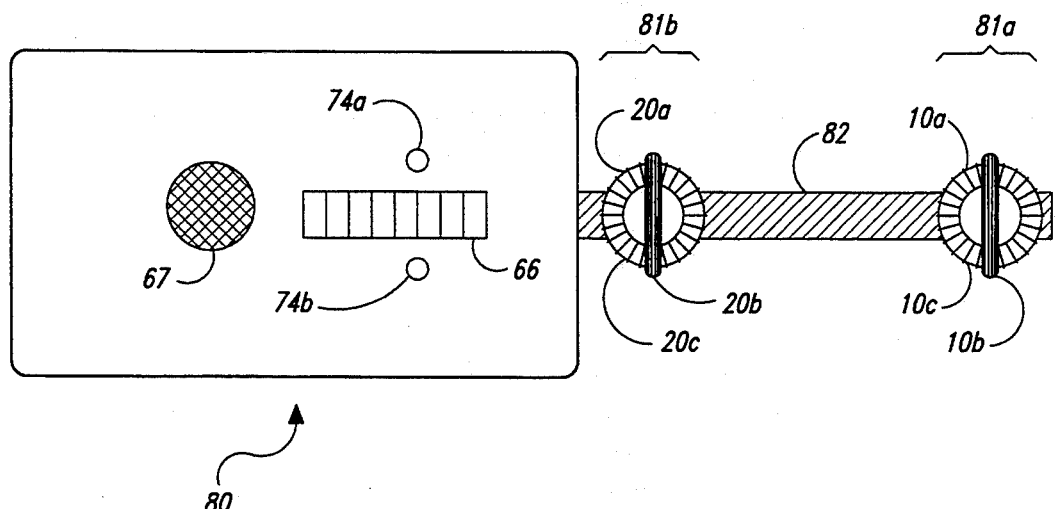
FIG. 3 illustrates an embodiment of a detection apparatus of this invention.

Referring to FIG. 3, each flux-gate toroidal sensor (81a) and (81b) comprises a 1 cm nickel-iron alloy toroid (10a) and (20a) with an excitation winding (10c) and (20c) and a detection winding (10b) and (20b). The excitation windings (10c) and (20c) are #37 gauge wire evenly wound in a toroidal manner around the perimeter of each toroid (10a) and (20a) such that the wire is closely spaced in a single layer. The detection windings (10b) and (20b) consist of #37 gauge wire closely wound around an outside diameter of each toroid (10a) and (20a). The flux-gate toroidal sensors (81a) and (81b) are fixed near each end of an 8 cm mounting arm (82), with their detection winding axes aligned and parallel to the length of the mounting arm.

Figure 2:
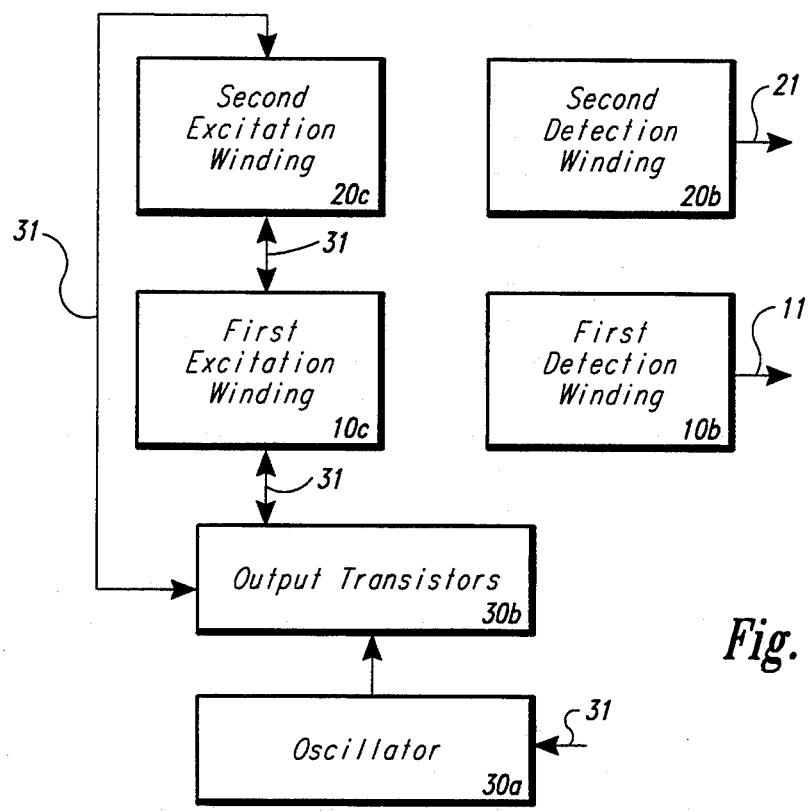
FIG. 2 is a block diagram illustrating an embodiment of the first and second sensor, as well as the sensor driver.

Referring to FIGS. 1 through 3, the sensor driver (30) for each flux-gate toroidal sensor (81a) and (81b) comprises an oscillator (30a) and output transistors (30b), which are alternately switched by the oscillator, allowing current to flow through the excitation windings (10c) and (20c) in alternating directions at the oscillator frequency. The load of the output transistors is set to allow the current to drive each toroid into magnetic saturation at the peak current values in both directions. The amplifiers (12) and (22) and integrators (14) and (24) receive the voltage developed across their respective detection windings (10b) and (20b) when the toroid is driven into and out of saturation, and then provide an integrated voltage which is proportional to any external static magnetic field flux passing through the toroid on an axis parallel to the winding axis of the detection windings. The amplifiers (12) and (22) are biased to remain within their dynamic range during operation of the detection apparatus, and to account for slight variations in the flux-gate toroidal sensors (81a) and (81b).

The differential amplifier (40) amplifies the difference between the integrated voltages from the integrators. The magnitude circuit (60) provides a voltage proportional to the magnitude of this difference voltage, and a polarity voltage coding the polarity of the difference voltage.

The visual display driver (62) includes an integrated circuit which drives a visual display (66), such as a 10-step light emitting diode bar array, depending on its input voltage. A polarity circuit (70) and a polarity display driver (72) drive one of two light emitting diodes (74a) and (74b), depending on the polarity voltage. A voltage-controlled oscillator chip generates a speaker-projected sound whose pitch is proportional to the input voltage. The 10-step bar array displays the magnitude of the magnetic field gradient detected by the flux-gate toroidal sensors, while one of the two light emitting diodes lights up to indicate the polarity of the gradient.

Example 2

Detection of a Feeding Tube

Figure 4:
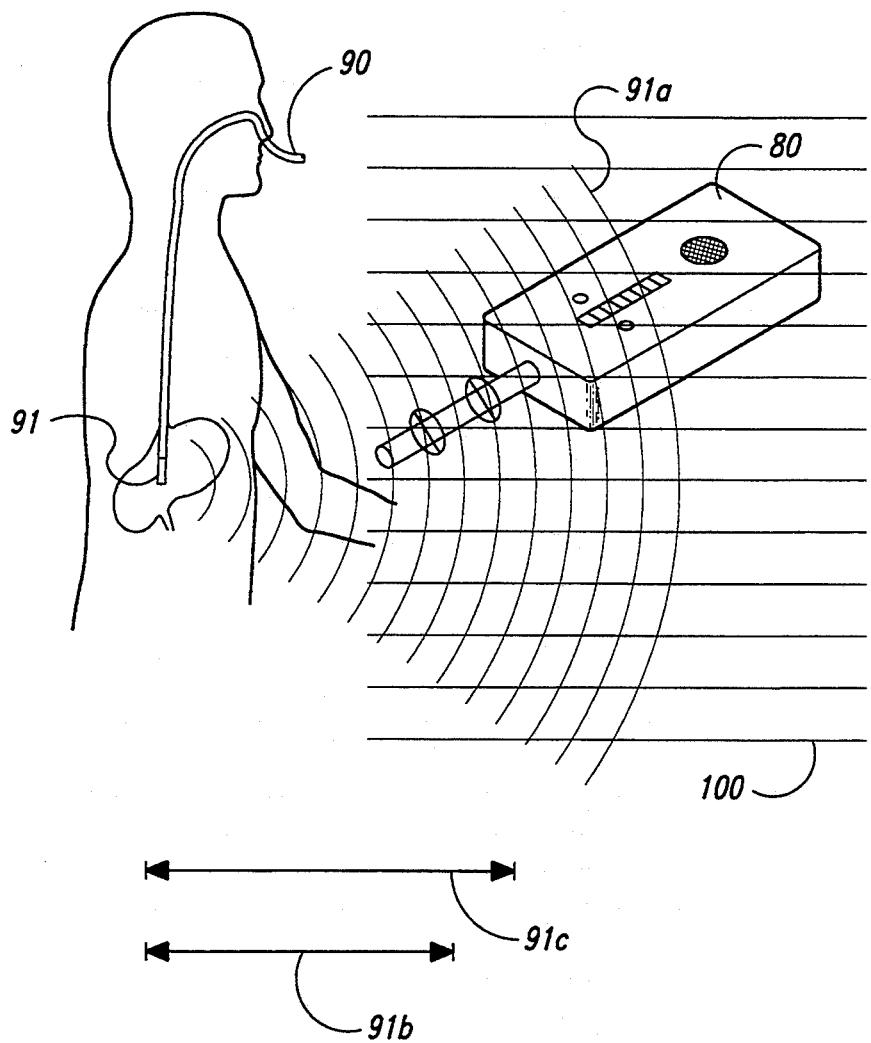
FIG. 4 illustrates the location of a magnet fixed to the end of a medical tube positioned within the body of a human patient using the detection apparatus of FIG. 3.

Referring to FIG. 4, a feeding tube (90), with a permanent magnet (91) located in its tip, includes an elongated, tubular, main portion with a sealed magnet chamber at its distal end, and an adapter at its proximal end to allow connection to a source of feeding formula. Side apertures at the distal end, above the magnet chamber, extend from the inner tube lumen to the exterior of the tube allowing the feeding formula to reach the patient's stomach. The sealed magnet chamber contains a cylindrical, rare earth, permanent magnet (91), of approximate size 0.10 inches diameter by 0.50 inches in length. The chamber is fused to the distal end of the feeding tube with its long axis parallel to the long axis of the feeding tube. The feeding tube and magnet chamber are composed of a flexible polymer which is chemically, biologically, and mechanically appropriate for purposes of gastroenteric feeding.

The feeding tube (90) is inserted into a patient's nose, down the esophagus and into the stomach. The detection apparatus (80) described in Example 1 above and illustrated in FIG. 3, is used to sense the magnet's static magnetic field strength (91a) at two different distances (91b) and (91c) while immersed in the earth's ambient magnetic field (100). As the detection apparatus (80) is moved about the patient's body, greater and lesser magnetic field gradients are indicated. The feeding tube (90) is located by moving the detection apparatus until the greatest magnitude is indicated by detection apparatus (80).

From the foregoing, it will be appreciated that, although specific embodiments of this invention have been described herein for purposes of illustration, various modifications may be made without deviating from the spirit and scope of the invention. Accordingly, the invention is not limited except by the appended claims.

We claim:

1. An apparatus for detecting the location of a magnet associated with a medical tube within the body of a patient, comprising:

means for sensing a first static magnetic field strength at a first distance from the magnet and providing a first sensor signal which is a function of the first static magnetic means for sensing a second static magnetic field strength at a second distance from the magnet and providing a second sensor signal which is a function of the second static magnetic field strength, wherein the second distance is greater than the first distance, wherein the means for sensing the first static magnetic field strength and providing the first sensor signal, and the means for sensing the second static magnetic field strength and providing the second sensor signal comprise a static magnetic field strength sensor driver for providing a driver signal, a first static magnetic field strength sensor for receiving the driver signal and thereby providing the first sensor signal, and a second static magnetic field strength sensor for receiving the driver signal and thereby providing the second sensor signal, wherein the static magnetic field strength sensor driver comprises an oscillator and output transistors which are alternately switchable by the oscillator and thereby provide the driver signal, wherein the first static magnetic field strength sensor comprises a first flux-gate toroidal sensor which includes a first excitation winding for receiving the driver signal and a first detection winding for providing the first sensor signal, and wherein the second static magnetic field strength sensor comprises a second flux-gate toroidal sensor which includes a second excitation winding for receiving the driver signal and a second detection winding for providing the second sensor signal;

means for receiving the first sensor signal and providing a first detection signal which is a function of the first sensor signal;

means for receiving the second sensor signal and providing a second detection signal which is a function of the second sensor signal;

means for receiving the first and second detection signals and providing a differential signal which is a function of the difference between the first detection signal and the second detection signal; and means for receiving and indicating a value for the differential signal.

2. An apparatus for detecting the location of a magnet associated with a medical tube within the body of a patient, comprising:

means for sensing a first static magnet field strength at a first distance from the magnet and providing a first sensor signal which is a function of the first static magnetic field strength;

means for sensing a second static magnetic field strength at a second distance from the magnet and providing a second sensor signal which is a function of the second static magnetic field strength, wherein the second distance is greater than the first distance;

means for receiving the first sensor signal and providing a first detection signal which is a function of the first sensor signal;

means for receiving the second sensor signal and providing a second detection signal which is a function of the second sensor signal;

means for receiving the first and second detection signals and providing a differential signal which is a function of the difference between the first detection signal and the second detection signal, wherein the means for receiving the first and second detection signals and providing the differential signal comprises a differential amplifier; and means for receiving and indicating a value for the differential signal.

3. An apparatus for detecting the location of a magnet associated with a medical tube within the body of a patient, comprising:

means for sensing a first static magnetic field strength at a first distance from the magnet and providing a first sensor signal which is a function of the first static magnetic field strength;

means for sensing a second static magnetic field strength at a second distance from the magnet and providing a second sensor signal which is a function of the second static magnetic field strength, wherein the second distance is greater than the first distance;

means for receiving the first sensor signal and providing a first detection signal which is a function of the first sensor signal;

means for receiving the second sensor signal and providing a second detection signal which is a function of the second sensors signal;

means for receiving the first and second detection signals and providing a differential signal which is a function of the difference between the first detection signal and the second detection signal; and means for receiving and indicating a value for the differential signal, wherein the means for receiving and indicating a value for the differential signal comprises a magnitude circuit for receiving the differential signal and providing a magnitude signal which is proportional to the magnitude of the differential signal, a visual display driver for receiving the magnitude signal and providing a visual display signal, and a visual display for receiving and visually indicating the visual display.

4. The apparatus of claim 3, wherein the visual display driver comprises a light emitting diode bar array driver, and the visual display comprises a light emitting diode bar array.

5. The apparatus of claim 3, wherein the means for receiving and indicating a value for the differential signal further comprises a tone generator for receiving the magnitude signal and providing a tone signal which is a function of the magnitude signal, and a speaker for receiving and audibly indicating the tone signal.

6. The apparatus of claim 3, wherein the means for receiving and indicating a value for the differential signal further comprises a polarity circuit for receiving the differential signal and providing a polarity signal which is a function of the polarity of the differential signal, a polarity display driver for receiving the polarity signal and providing a polarity display signal, and a polarity display for receiving and visually indicating the polarity display signal.

7. An apparatus for detecting the location of a magnet associated with a medical tube within the body of a patient, comprising:

means for sensing a first static magnetic field strength at a first distance from the magnet and providing a first sensor signal which is a function of the first static magnetic field strength;

means for sensing a second static magnetic field strength at a second distance from the magnet and providing a second sensor signal which is a function of the second static magnetic field strength, wherein the second distance is greater than the first distance;

means for receiving the first sensor signal and providing a first detection signal which is a function of the first sensor signal;

means for receiving the second sensor signal and providing a second detection signal which is a function of the second sensor signal;

means for receiving the first and second detection signals and providing a differential signal which is a function of the difference between the first detection signal and the second detection signal;

means for receiving and indicating a value for the differential signal; and means for automatically controlling, monitoring and calibrating the means for sensing the first static magnetic field strength and providing the first sensor signal, the means for sensing the second static magnetic field strength and providing the second sensor signal, the means for receiving the first sensor signal and providing the first detection signal, the means for receiving the second sensor signal and providing the second detection signal, the and means for receiving and indicating a value for the differential signal.

8. The apparatus of claim 7, wherein the automatic controlling, monitoring, and calibrating means comprises a microprocessor.

9. A method of detecting the location of a magnet associated with a medical tube within the body of a patient, comprising:

sensing a first static magnetic field strength at a first distance from the magnet;

sensing a second static magnetic field strength at a second distance from the magnet which is greater than the first distance;

providing a first sensor signal which is a function of the first static magnetic field strength;

providing a second sensor signal which is a function of the second static magnetic field strength;

receiving the first and second sensor signals and providing a differential signal which is a function of the difference between the first static magnetic field strength and the second static magnetic field strength;

receiving and indicating a value for the differential signal; and determining the location of the medical tube by varying the first and second distances until the greatest value for the differential signal is indicated.

10. A method of verifying the location of a magnet associated with a medical tube within the body of a patient, comprising:

sensing a first static magnetic field strength at a first distance from the magnet;

sensing a second static magnetic field strength at a second distance from the magnet which is greater than the first distance;

providing a first sensor signal which is a function of the first static magnetic field strength;

providing a second sensor signal which is a function of the second static magnetic field strength;

receiving the first and second sensor signals and providing a differential signal which is a function of the difference between the first static magnetic field strength and the second static magnetic field strength;

receiving and indicating the polarity of the differential signal; and manipulating the magnet until the indicated polarity of the differential signal changes.

11. The method of claim 10, wherein manipulating the magnet is accomplished by rotation thereof.

12. An apparatus for detecting the location of a magnet associated with a medical tube within the body of a patient, comprising:

a static magnetic field strength sensor driver for providing a driver signal;

a first static field strength sensor coupled to the static magnetic field strength sensor driver for receiving the driver signal and thereby providing a first sensor signal which is a function of a first static magnetic field strength at a first distance from the magnet;

a second static magnetic field strength sensor coupled to static magnetic field strength sensor driver for receiving the driver signal and thereby providing a second sensor signal which is a function of a second static magnetic field strength at a second distance from the magnet, wherein the second distance is greater than the first distance;

a first amplifier coupled to the first static magnetic field strength sensor for receiving the first sensor signal and providing a first amplified signal which is proportional to the first sensor signal;

a first integrator coupled to the first amplifier for receiving the first amplified signal and providing a first detection signal which is a function of the first sensor signal;

a second amplifier coupled to the second static magnetic field strength sensor for receiving the second sensor signal and providing a second amplified signal which is proportional to the second signal;

a second integrator coupled to the second amplifier for receiving the second amplified signal and providing a second detection signal which is a function of the second sensor signal;

a differential amplifier coupled to the first and second integrators for receiving the first and second detection signal and providing a differential signal which is a function of the difference between the first detection signal and the second detection signal;

a magnitude circuit coupled to the differential amplifier for receiving the differential signal and providing a magnitude signal which is proportional to the magnitude of the differential signal;

a visual display driver coupled to the magnitude circuit for receiving the magnitude signal and providing a visual display signal; and a visual display coupled to the visual display driver for receiving and visually indicating the visual display signal.

13. The apparatus of claim 12, wherein the static magnetic field strength sensor driver comprises an oscillator and output transistors which are alternately switchable by the oscillator and thereby provide the driver signal, wherein the first static magnetic field strength sensor comprises a first flux-gate toroidal sensor which includes a first excitation winding for receiving the driver signal and a first detection winding for providing the first sensor signal, and wherein the second static magnetic field strength sensor comprises a second flux-gate toroidal sensor which includes a second excitation winding for receiving the driver signal and a second detection winding for providing the second sensor signal.

14. The apparatus of claim 12, wherein the visual display driver comprises a light emitting diode bar array driver, and the visual display comprises a light emitting diode bar array.

15. The apparatus of claim 12, further comprising a tone generator coupled to the magnitude circuit for receiving the magnitude signal and providing a tone signal which is a function of the magnitude signal, and a speaker coupled to the tone generator for receiving and audibly indicating the tone signal.

16. The apparatus of claim 12, further comprising a polarity circuit coupled to the differential amplifier for receiving the differential signal and providing a polarity signal which is a function of the polarity of the differential signal, a polarity display driver coupled to the polarity circuit for receiving the polarity signal and providing a polarity display signal and a polarity display coupled to the polarity display driver for receiving and visually indicating the polarity display signal.

17. The apparatus of claim 12, further comprising a microprocessor coupled to the static magnetic field strength sensor driver, the first amplifier, the second amplifier, the differential amplifier, and the visual display driver for automatically controlling, monitoring and calibrating the static magnetic field strength sensor driver, the first amplifier, the second amplifier, the differential amplifier, and the visual display driver.

* * * * *

UNITED STATES PATENT AND TRADEMARK OFFICE
CERTIFICATE OF CORRECTION

PATENT NO.    : 5,425,382
DATED         : June 20, 1995
INVENTOR(S)   : Robert N. Golden and Fred E. Silverstein It is certified that error appears in the above identified patent and that said Letters Patent is hereby corrected as shown below:

In column 10, claim 1, line 34, after "magnetic", please insert --field strength;--.

In column 11, claim 2, line 13, please delete "magnet" and substitute therefore --magnetic--.

In column 12, claim 7, line 55, please delete "the and" and substitute therefore --and the--.

In column 14, claim 12, line 11, please delete the first occurrence of "signal" and substitute therefore --signals--.

Signed and Sealed this

Twenty-eighth Day of November 1995

Attest:

BRUCE LEHMAN

*Attesting Officer*       *Commissioner of Patents and Trademarks*